United States Patent [19]

Fuchigami et al.

[11] Patent Number: 5,356,867
[45] Date of Patent: Oct. 18, 1994

[54] METHOD AND COMPOSITION COMPRISING VINYL OR VINYLIDENE HALIDE POLYMERS FOR CONTROLLING WATER LOSS IN PLANTS

[75] Inventors: Leslie H. Fuchigami, Corvallis, Oreg.; Darrell Badertscher, Washougal, Wash.

[73] Assignee: State of Oregon Acting By And Through the Oregon State Board of Higher Education on Behalf of Oregon State Univeristy, Eugene, Oreg.

[21] Appl. No.: 866,046

[22] Filed: Apr. 8, 1992

[51] Int. Cl.$^5$ ............................................. A01N 29/02
[52] U.S. Cl. ................................ 504/356; 71/DIG. 1
[58] Field of Search ............... 71/126, DIG. 1, 65; 504/356, 116

[56] References Cited

U.S. PATENT DOCUMENTS

| | | | |
|---|---|---|---|
| 3,791,839 | 2/1974 | Cushman et al. | 106/268 |
| 3,819,530 | 6/1974 | Rutledge et al. | 252/311.5 |
| 3,826,671 | 7/1974 | Petrucco et al. | 117/3 |
| 3,847,641 | 11/1974 | Cushman et al. | 117/3 |
| 3,890,158 | 6/1975 | Cushman et al. | 106/271 |
| 4,058,409 | 11/1977 | Kesslin | 106/271 |
| 4,155,892 | 5/1979 | Emmons et al. | 504/116 |
| 4,604,129 | 8/1986 | Schott et al. | 504/180 |
| 4,943,315 | 7/1990 | Schulz et al. | 71/120 |
| 4,985,062 | 1/1991 | Hughes | 71/77 |
| 5,160,527 | 11/1992 | Law et al. | 504/156 |

FOREIGN PATENT DOCUMENTS

| | | |
|---|---|---|
| 212628 | 12/1960 | Austria . |
| 123052 | 7/1901 | Fed. Rep. of Germany . |
| 397164 | 1/1974 | U.S.S.R. . |
| 1491429 | 7/1989 | U.S.S.R. . |

*Primary Examiner*—Richard L. Raymond
*Assistant Examiner*—S. Mark Clardy
*Attorney, Agent, or Firm*—Klarquist Sparkman Campbell Leigh & Whinston

[57] ABSTRACT

A liquid composition is applied to a plant to provide a barrier to water vapor transmission. The composition dries to form a film on the surface of the plant. The film inhibits water loss and thereby increases the survival likelihood and quality of the plant.

A particularly suitable coating composition comprises: from about forty to about ninety-five weight percent of a vinyl chloride or vinylidene chloride polymer; from about 1.0 to about 2.0 weight percent of a coalescing agent such as 2,2,4-trimethyl-1,3-pentanediol monoisobutyrate; about 0.5 to about 1.0 weight percent of a surfactant such as a polyoxypropylene-polyoxyethylene copolymer; about 0.5 to about 1.0 weight percent of a viscosity increasing agent such as a urethane copolymer; and from about 0.3 to about 1.0 weight percent of a defoaming agent, such as silica.

24 Claims, No Drawings

METHOD AND COMPOSITION COMPRISING VINYL OR VINYLIDENE HALIDE POLYMERS FOR CONTROLLING WATER LOSS IN PLANTS

FIELD OF THE INVENTION

This invention is directed to a composition that is applied to the surface of a plant to reduce the plant's water loss.

BACKGROUND OF THE INVENTION

Plants experience stress from excessive water loss (water or desiccation stress), and a major factor contributing to the loss of nursery stock is water stress. Some plants, such as the Washington hawthorn, are quite sensitive to water loss. For example, Washington hawthorns that experience water stress for 48 hours have a survival rate of about ten percent, and the plants that do survive have limited root growth. Other plants, such as the Norway Maple, are less sensitive to the effects of water loss, although they also are damaged by excessive water loss. Therefore, limiting the plant damage or plant loss associated with water stress is a significant concern for businesses that require healthy, attractive plants. By preventing water stress throughout post-harvest handling and plant establishment periods, good survival and plant growth can occur.

Antitranspirant coating compositions that reduce water loss from the surface of plants have been described in previous U.S. patents. For instance, U.S. Pat. No. 3,826,671 describes a method for controlling water transpiration from plants using a composition comprising an aqueous emulsion of, by weight, 5-50 percent polyethylene, 2-10 percent of an emulsifier, and a minor portion of wax. U.S. Pat. No. 4,058,409 describes an antitranspirant composition that consists essentially of: (1) an aqueous emulsion of oxidized, emulsifiable polyethylene having molecular weights of about 1000 to about 3400 daltons; and (2) at least 25% polyterpene having molecular weights in the range of about 600 to about 1800 with an acid number of zero. Finally, U.S. Pat. No. 4,943,315 describes an antitranspirant composition that comprises a mixture of an acetylene derivative and a phenylbenzylurea derivative. Antitranspirant compositions, including wax-based compositions, are also commercially available. Many of these antitranspirant compositions include active or inert ingredients in addition to the antitranspirant agent.

Although prior plant coating agents generally reduce a plant's water loss, many permit water loss at a rate detrimental to plants experiencing water stress for extended periods. As a result, prior coating agents have little or no beneficial effect on the survival and growth of desiccation-sensitive plants. Furthermore, procedures for reducing water loss may be effective, but are either difficult to use on a commercial scale or with large plants, such as shrink-wrapping, or inhibit the transmission of essential respiratory or photosynthetic gases. As a result, plants coated with prior coating compositions and experiencing water stress still have low survival rates, extensive dieback (the percent of the plant, measured from the top of the plant to the root, that has dried perceptively) and unsatisfactory new root growth. Therefore, there has long been a need for a plant coating composition that: (1) is easily and uniformly applied to large numbers of plants; (2) reduces water vapor transmission rates; (3) increases plant survival rates and new root growth and decreases dieback following water stress; and (4) is non-phytotoxic.

SUMMARY OF THE INVENTION

The present invention is directed to a plant coating composition and a process for using the composition that addresses the problems associated with previous antitranspirant compositions.

The compositions of the present invention are superior to prior coating compositions in increasing plant survival rate and new root growth, and decreasing dieback after the plant experiences water stress.

The coating compositions of the present invention comprise water and a polymer material having monomer subunits of the formula $H_2C=CR_1R_2$, wherein R1 is selected from the group consisting of halogens, and R2 is selected from the group consisting of hydrogen and halogens. Particular monomer subunits satisfying this formula are vinyl or vinylidene chloride.

A particularly suitable embodiment of the plant coating composition comprises: (1) from about forty to about ninety-five weight percent of a vinyl chloride polymer; (2) from about 1.0 to about 2.0 weight percent of 2,2,4-trimethyl-1,3-pentanediol monoisobutyrate (a coalescing agent); (3) from about 0.5 to about 1.0 weight percent of a polyoxypropylene-polyoxyethylene copolymer (a surfactant); (4) from about 0.5 to about 1.0 weight percent of a urethane copolymer (a viscosity enhancing agent); (5) from about 0.3 to about 1.0 weight percent of a colloidal agent such as silica (a defoaming agent); and (6) the remaining weight percent is water.

A thin, uniform film of the plant coating composition is formed on the surface of a plant by substantially coating the plant's surface with the composition using methods known in the art such as, without limitation, spraying, painting or dipping and allowing the composition to dry. When applied to tree stems, the coating compositions of the present invention reduce the water vapor transmission rates from about 2 to about 5 times the vapor transmission rates of tree stems not coated with the composition. Plants coated with the present compositions have water vapor transmission rates that are from about 1.5 to about 3.0 times lower than the transmission rates of plants not coated with the compositions.

The coating compositions of the present invention are superior to prior coating compositions. The average water vapor transmission rate of maple stems coated with prior compositions was 17.3 mg.cm$^{-2}$.96 h$^{-1}$, and 23.6 mg.cm$^{-2}$.96 h$^{-1}$ for hawthorn tree stems. These average values are 3.3 and 4.2 times higher than the water vapor transmission rates of maple and hawthorn tree stems coated with the compositions of the present invention having from about eighty-five to about ninety-five weight percent polymer material (defined to be "undiluted"), and 1.8 and 2.4 times the transmission rates of maple and hawthorn tree stems coated with the present compositions having from about forty to about eighty-five weight percent polymer material (defined to be an aqueous emulsion of the coating composition).

Moreover, the survival rate, new root growth and decrease in plant dieback for plants coated with the compositions of the present invention and thereafter experiencing water stress are superior to values obtained in comparative tests with prior antitranspirant coating compositions. The percent dieback of a Washington hawthorn coated with compositions of the present invention having from about eighty-five to about ninety-five weight percent polymer material is about 23 percent after a water-stress period of 48 hours. The next-closest prior antitranspirant agent in terms of dieback values is about 87 percent. The average percent dieback for Washington hawthorns coated with prior compositions was about 91 percent, or about 4.0 times the value for undiluted compositions of the present invention and 2.1 times the value for aqueous emulsions. The root ratings of Washington hawthorns coated with the present coating compositions and repotted after experiencing 48 hours of water stress are about 1.5 times better than the next closest competitor, and about 2.2 times the average root rating. In similar tests with large hawthorn trees and with other plant materials such as conifer seedlings, Christmas trees, perennials and annuals, the coating compositions of the present invention greatly reduced water loss and improved the survival of the plant materials tested. In all tests conducted, the coating compositions were not toxic to foliage, stems or roots and allowed some gas exchange to occur.

DETAILED DESCRIPTION OF THE INVENTION

The plant coating compositions of the present invention comprise from about forty to about ninety-five weight percent (based on the total weight of the composition) of a polymer that is formed from monomer subunits having the formula $H_2C=CR_1R_2$. The $R_1$ substituent is selected from the group consisting of halogens, and the $R_2$ substituent is selected from the group consisting of hydrogen and halogens. The monomer subunits may have any combination of $R_1$ and $R_2$ (hydrogen and halogen). Without limitation, preferred embodiments of monomer subunits within the scope of the present invention include: (1) $R_1=Cl$, $R_2=H$ (vinyl chloride); and (2) $R_1=R_2=Cl$ (vinylidene chloride). A particularly suitable monomer subunit is vinyl chloride, and a particularly suitable coating composition comprises from about eighty-five to about ninety-five weight percent polymeric vinyl chloride.

One skilled in the art will realize that chlorine can be replaced in the vinyl or vinylidene halogen polymers by another halogen and still be within the scope of the present invention. Thus, the following monomer subunits, without limitation, also are within the scope of the present invention: $H_2C=ClCl$, $H_2C=CFCl$, $H_2C=CBrCl$, $H_2C=Cl_2$, $H_2C=CCl_2$, $H_2C=CF_2$, $H_2C=CBr_2$, $H_2C=CHF$, $H_2C=CHCl$, $H_2C=CHBr$, and $H_2C=CHI$.

Many of the vinyl or vinylidene halogen polymers useful for the present compositions can be purchased. For instance, a particularly suitable example of a commercially available vinyl halogen polymer is sold as "HALOFLEX 202," a vinyl chloride polymer manufactured by ICI Americas, Inc. of Wilmington, Md. This material is a milky white liquid with an average particle size of 0.2 microns. It has a pH of 1-2 and is anionic. The minimum film formulation temperature is 12°-15° C. and the glass transition temperature is 0° C. It has a viscosity of 20 centipoise and a density of 13.2 pounds per gallon. It is about 60% solids by weight and about 50% solids by volume, with the volatile portion of the emulsion being water. Dilution of this emulsion causes it to provide a thinner film. It performs correctly when dried in the temperature range of 45° F. to 110° F.

The plant coating compositions of the present invention typically include one or more compounds in addition to water and the vinyl or vinylidene halogen polymers. The coating compositions can also include additives such as salts, defoaming agents, surfactants, coalescing agents, and viscosity enhancing agents and still be within the scope of the present invention.

A defoaming agent is typically added to the coating compositions of the present invention to facilitate the formation of a uniform film on the plant's surface. The process of the present invention is most effective when the entire surface of the plant is substantially covered with a uniform film. The amount of the coating composition required to form a uniform, thin (less than about 3-5 mm) film on the entire surface of the plant is defined to be an effective amount of the composition. Compositions that foam or otherwise entrain air to form bubbles do not form a substantially uniform film on the surface of a plant because the bubbles break and form regions on the plant's surface devoid of coating composition. The plant will experience excessive water loss from these regions. Thus, any defoaming agent is within the scope of the present invention that prevents foaming or bubble formation and allows a substantially continuous, uniform coating of the coating composition to be applied to the plant's surface. A particular embodiment of the present invention uses a colloidal agent to reduce foaming and thereby facilitate uniform films. A particularly suitable embodiment of the present invention uses "COLLOIDS 640," a colloidal agent manufactured by Colloids of California, Inc. of Richmond, Calif. The defoaming agent, such as "COLLOIDS 640," is typically included in the plant coating compositions at a weight percent of from about 0.03 to about 1.0 weight percent, such as about 0.65 weight percent, based on the total weight of the coating composition.

The coating compositions of the present invention may also include surfactants. Surfactants reduce the surface tension of the compounds comprising the plant coating compositions and thereby increases the miscibility of the compounds. It will be understood by one skilled in the art that any surfactant or miscibility agent that does not interfere with the antitranspirant agent's function or render the composition phytotoxic is within the scope of the present invention. Particular surfactants for the present invention comprise polyoxyalkylene compounds and mixtures of such compounds. A particular suitable embodiment of the present invention uses a surfactant sold under the trade name "PLURONIC F-87," which is sold by BASF Corporation Chemicals Division, of Parsippney, N.J. "PLURONIC F-87" surfactant is a polyoxypropylenepolyoxyethylene copolymer. Surfactants such as the "PLURONIC F-87" surfactant are typically added to the coating composition in a weight percent of from about 0.5 to about 1.5 weight percent, such as about 1 percent.

The coating compositions of the present invention can also include coalescing agents. A coalescing agent facilitates the formation of a uniform film on the plant's surface under ambient temperature and humidity conditions. Plants are typically grown or stored in environments having temperatures and humidity conditions that are not ideal for drying film-forming coating compositions. For instance, latex films which, when applied to plants, allow little water transmission but also cause tissue browning created by the complete prevention of gas exchange, require temperatures approaching 100° F. in order for the composition to properly dry and form a film. A coalescing agent is added to the coating compositions of the present invention to reduce the temperature required to form a film on the plant's surface. Suitable coalescing agents for the present invention are those that lower the film-forming temperature (or the $P_g$ of the film; $P_g$ is the glass transition temperature) of the coating composition to below 100° F. More preferably, the coalescing agent should lower the film-forming temperature to about 40° F. A particularly suitable coalescing agent for the present invention is 2,2,4-trimethyl-1,3-pentanediol monoisobutyrate. This coalescing agent is sold as "TEXANOL" by Van Waters & Rogers, Inc. If a coalescing agent is used with the plant coating compositions of the present invention, it is typically added in an amount of from about 1.5 to about 2.5 weight percent, such as about 2 percent.

Viscosity increasing agents can also be added to the coating compositions of the present invention. Without an added viscosity increasing agent, the coating compositions typically have a viscosity similar to water. The coating compositions remain on a plant's surface longer, and especially until the composition drys, if the viscosity of the composition is increased. The viscosities of the compositions were increased by adding agents that either cross-link or add to the length of the vinyl or vinylidene halogen polymer chains. Without limiting the present invention to one proposed method of operation, the antitranspirant polymers of the present invention are believed to have reactive hydroxyl groups that react with the viscosity increasing agents to either extend the length of a halogenated polymer chain, or to cross-link separate halogenated polymer chains. Particular viscosity increasing agents for the present invention include urethane copolymers. A particularly suitable embodiment of a viscosity enhancing agent useful for the present invention is "BERMODOL PUR-2100," manufactured by Berol Chemicals, Inc., Box 851, S-444 01, Stenunsgund, Sweden. When a viscosity agent is added to the coating compositions of the present invention, it is typically added in an amount from about 0.5 to about 1.5 weight percent, such as about 1 percent by weight.

Particularly useful coating compositions according to the present invention are shown below in Table 1 and Table 2, wherein the weights are expressed in pounds. Table 1 lists weight percents comprising full-strength coating compositions and Table 2 lists weight percents within the emulsion concentrations suitable for the present invention.

TABLE 1

| Agent | Weight | Wt. % |
|---|---|---|
| Water | 75.06 | 6.5 |
| PLURONIC F-87 | 12.00 | 1.0 |
| TEXANOL | 23.73 | 2.0 |
| HAIDFLEX 202 | 1029.99 | 88.8 |
| BERMODOL-PUR2100 | 11.15 | 0.96 |
| COLLOIDS 640 | 7.5 | 0.65 |
| Total Weight | 1159.43 | 100.0 |

TABLE 2

| Agent | Weight | Wt. % |
|---|---|---|
| Water | 1234.49 | 53.23 |
| PLURONIC F-87 | 12.00 | 0.53 |
| TEXANOL | 23.73 | 1.0 |
| HALOFLEX 202 | 1029.99 | 44.43 |
| BERMODOL-PUR2100 | 11.15 | 0.48 |
| COLLOIDS 640 | 7.5 | 0.33 |
| Total Weight | 2318.86 | 100.0 |

Particularly suitable coating compositions of the present invention have been formulated, either batchwise or continuously, using the weight percents shown in Table 1 or Table 2. Example 1 provides a specific example of how a "undiluted" coating composition of the present invention was made.

EXAMPLE 1

A first mixture is formed by combining:
(1) 41.70 pounds of water (5.00 gallons);
(2) 12.00 pounds of "PLURONIC F-87," a polyoxypropylene-polyoxythylene block copolymer (1.38 gallons; 1.0 weight percent); and
(3) 23.73 pounds of "TEXANOL," 2,2,4-trimethyl1,3-pentanediol monoisobutyrate (3.00 gallons; 2.0 weight percent).

The first mixture is vigorously mixed using any means known in the art such as mechanical or ultrasonic agitation. The following compounds are then added to the first mixture with agitation:
(1) 1,029.99 pounds of "HALOFLEX 202" (95.00 gallons; 88.8 weight percent);
(2) 11.15 pounds of "BERMODOL-PUR-2100" (1.25 gallons; 0.96 weight percent);
(3) 7.50 pounds "COLLOIDS 640" (1.00 gallon; .65 weight percent) of; and
(4) 33.36 pounds of water (4.00 gallons; total weight percent of water is 6.5 weight percent).

A vinylidene chloride polymer can be substituted for the vinyl chloride polymer ("HALOFLEX 202") discussed above. Similarly, other vinyl or vinylidene halogen polymers can be substituted for the vinyl chloride polymer shown in Example 1 and still be within the scope of the present invention. Moreover, additives that function as coalescing agents, surfactants, defoaming agents or viscosity increasers and that differ from the compounds described above can also be used.

To coat plants, the coating compositions are thoroughly mixed and then an effective amount of the composition is applied to the surface of a plant so that the plant surface is substantially coated with the coating composition. The coating composition can be applied to plants either undiluted, i.e., without being diluted with a diluent such as water, or as an emulsion wherein the polymer material has a weight percent of about forty to about eighty-five percent. However, the coating composition may be used in the form of an emulsion having lower weight percents of the polymer material as long as the emulsion is suitable for applying an amount of polymer material sufficient to reduce the plant's water vapor transmission, preferably by a single application. The best dilution for a particular type of plant can be determined by experimentation.

The coating composition can be applied to the plant in a number of ways well-known in the art. Without limitation, the coating composition may be applied by spraying, dipping, painting, roll coating, etc. The coating compositions were applied to the surface of the plant and allowed to dry under ambient temperature and humidity conditions for a period sufficient to form a uniform, thin 0.25 to 1 mil film on the surface of the plant. Temperature and humidity have an effect on drying time. For example, drying occurs in about 15 to 30 minutes at 60° F. and 50% relative humidity or in about 6 to 12 hours at 45° F. and 80% relative humidity. Drying time is also effected by the extent of air movement, exposure to sunlight and other factors. During drying, the composition changes color from a milky white to a bluish color and finally becomes clear. Clearness is a good indicator of when the coating composition has dried. The coating compositions of the present invention are particularly suited for reducing the transmission of water vapor from the surface of plants and thereby reducing the attendant water stress. Surprisingly, plants coated with the compositions of the present invention and thereafter experiencing water stress, such as may occur during transport or transplant of the plants, have increased survival rates, superior new root growth, and decreased dieback when compared to plants coated with previous coating compositions. Although the coating compositions of the present invention can be used with all types of plants, testing has focused on bare-rooted dormant deciduous trees. Bare-rooted dormant deciduous trees were used because such trees may, for example, experience severe water stress during post harvest handling in the nursery industry. The Washington hawthorn was selected to test the coating compositions of the present invention because it is representative of plants that are highly sensitive to water loss. Other trees, such as the Norway maple, are more tolerant to water loss, and the Norway maple was selected as an example of such a plant.

Two types of experiments were performed to test the effectiveness of the present compositions as plant coating compositions: first, stem sections from maple and hawthorn trees were used to compare the water vapor transmission rates of plants coated with the present coating compositions relative to a control not coated with the compositions and to plants coated with prior coating compositions; second, maple and hawthorn seedlings were used to compare the survival rate, new root growth and dieback in plants subjected to and surviving water stress when coated with the compositions of the present invention, relative to maple and hawthorn seedlings not coated with the compositions and when coated with prior antitranspirants.

For the stem-sections test, a 10 centimeter stem section was selected from either a Norway maple tree or a Washington hawthorn tree. The 10 centimeter stem sections were sealed on the cut ends with melted paraffin wax and then immersed in each coating composition tested. The coating composition was allowed to dry and form a film on the stem, and then the coated stem was weighed. The coated stem sections were air dried (at approximately $23 \pm 2°$ C., $47 \pm 5\%$ relative humidity) on a laboratory bench for 96 hours and then reweighed to determine the amount of water lost during air drying. The plant stem diameter was measured to determine the bark's surface area, and water loss rate was expressed as the amount of water lost per unit of surface area per unit time, i.e., milligrams of $H_2O.cm^{-2}.96\ h^{-1}$. Water loss rate was determined using the following formula:

$$\text{Water loss rate} = \frac{\text{Initial wt. (0 hrs.)} - \text{Final wt. (96 hrs.)}}{\text{Stem surface area (cm}^2\text{)} \times \text{Time}}$$

The data obtained from the 10 centimeter stem section tests was analyzed using a statistical program to determine if the experimental results were statistically significant. The relative statistical significance of the data is represented using small letters a-g. The letters a-g are shown following the experimentally determined values listed in Table 3 and indicate whether the experimental data is statistically significant for the data points obtained. If the letters are identical for two different trials, then the results are not deemed significant at a confidence level of 0.05. If a different letter or group of letters appears next to an experimental value relative to another compound of interest, then the experimentally derived data is deemed to be statistically significant. For instance, the vapor transmission value for the maple control is 23.2 mg $_2$O. $cm^{-2}.96\ h^{-1}$ and is followed by an "a." The value for "MOISTURIN" coating composition (the term used herein to designate the compositions of the present invention) is 5.3 mg $H_2O\ cm^{-2}.96\ h^{-1}$ and is followed by "c." Therefore, the difference between the two experimentally determined values is considered to be statistically important.

In Table 3, the preferred coating composition of the present invention, listed as "MOISTURIN" in the tables that follow, was applied undiluted or as an emulsion. The values in the 10 cm stem sections not coated with the composition are, for the maple and hawthorn stems respectively, 23.2 mg $H_2O.cm^{-2}.96\ h^{-1}$ and 28.2 mg $H_2O.cm^{-2}.96^{-1}$. Table 3 shows that stems coated with undiluted "MOISTURIN" coating composition had a water transmission vapor rate that was reduced to 5.3 and 5.6 mgs $H_2O.cm^{-2}.96\ h^{-1}$, i.e., from about 4.4 times to about 5.0 times the vapor transmission rate experienced by the maple and hawthorn controls, respectively. Similarly, when "MOISTURIN" coating composition was applied as an emulsion, the vapor transmission rates were reduced to 9.8 and 9.7 mg $H_2O.cm^{-2}.96\ hr^{-1}$, i.e., 2.7 times and 2.9 times lower than the control values for the maple and hawthorn stem sections, respectively. Thus, the coating composition of the present invention reduces the water vapor transmission rates dramatically relative to uncoated plants. More specifically, the coating composition reduces the water vapor transmission from about 2.3 to about 5.0 times the control value.

Table 3 compares the preferred coating compositions of the present invention to a number of commercially available antitranspirant compositions and shows that the compositions of the present invention are superior to the prior antitranspirant coating compositions. For the maple stem sections tests, undiluted "MOISTURIN" coating composition reduced the water vapor transmission rate from about 2.0 times to about 4.2 times the values determined experimentally for the other antitranspirant compositions, and from about 1.1 times to about 2.3 times the values for the other antitranspirant compositions when "MOISTURIN" coating composition was applied as an emulsion. The average water transmission rate for maple stems coated with prior compositions is about 17.3 mg $H_2O.cm^{-2}.96\ h^{-1}$, or 3.3 times the value for undiluted compositions of the present invention, and about 1.8 times the value for the present compositions applied as an emulsion.

Similarly, for the hawthorn tree stem section tests, undiluted "MOISTURIN" coating composition reduced the water vapor transmission rate from about 2.6 times to about 5.3 times the values determined experimentally for the other antitranspirant compositions, and from about 1.5 times to about 3.1 times the values for the other antitranspirant compositions when "MOISTURIN" coating composition was applied as an emulsion. The average water transmission rate for hawthorn stems coated with prior compositions was about 23.6 mg $H_2O.cm^{-2}.96\ h^{-1}$. Undiluted "MOISTURIN" coating composition reduced the water vapor transmission rate nearly 4.2 times this value, and 2.4 times this value when applied as an emulsion. Thus, the preferred coating composition of the present invention is from about 1 to about 5 times more effective in reducing the water vapor transmission rate in plants coated with the composition than are previous antitranspirant coating agents.

TABLE 3

Water loss from maple and hawthorn item sections treated with antidesiccant compounds prior to air-drying.[z,y]

| | Water Loss Rate (mg water · cm$^{-2}$ · 96 h$^{-1}$) | |
|---|---|---|
| Treatment | Maple | Hawthorn |
| control | 23.2 a | 28.2 ab |
| ANTISTRESS 2000 (1:100) | 21.7 a | 25.9 ab |
| CLEARSPRAY | 18.5 ab | 23.3 abcde |
| CLOUDCOVER | 21.2 a | 29.4 a |
| FOLICOTE | 22.2 a | 23.6 abcde |
| FOREVERGREEN | 18.4 ab | 27.2 ab |
| NEEDLEHOLD | 19.0 ab | 27.1 ab |
| VAPORGARD | 15.5 abc | 24.2 abcd |
| WILTPRUF | 16.2 ab | 29.6 ab |
| DECCO A | 18.3 ab | 29.9 a |
| DECCO C | 13.2 abc | 25.2 abc |
| DECCO D | 17.6 ab | 21.4 bcdef |
| FRESH-COTE CW1 | 13.9 abc | 16.0 efg |
| FRESH-COTE 214 | 18.0 ab | 17.7 cdef |
| SEMPERFRESH | 21.6 a | 27.5 ab |
| SHIELD BRITE AP-50C | 15.4 abc | 24.0 abcd |
| SHIELD BRITE C-280 | 14.3 abc | 14.8 fg |
| STAFRESH 819 | 16.1 ab | 21.2 bcdef |
| BPC #1 | 10.4 bc | 16.8 defg |
| MOISTURIN (undiluted) | 5.3 c | 5.6 h |
| MOISTURIN (emulsion) | 9.8 bc | 9.7 gh |

[z]Water loss during 96 h air-drying at 23 ± 2° C., 47 ± 5% RH.
[y]Mean separation within columns by Tukey's multiple range test, P = 0.05

"MOISTURIN" coating composition was also used to test the survival rates and quality of whole-plant seedlings that are obtained when coated with "MOISTURIN" coating composition and then subjected to water stress. Bare-rooted Norway maple seedlings and bare-rooted Washington hawthorn seedlings were used in the whole-plant tests. The bare-rooted seedlings were dipped, including the whole plant, roots and shoot, in each of the antitranspirant compositions. The seedlings were then allowed to surface dry and the coated seedlings were then weighed. The coated seedlings were then air dried (23±2° C., 47±5% relative humidity) for 48 hours. Previous studies have shown that 48 hours of drying significantly reduces the survival rate of uncoated maples and uncoated hawthorn seedlings. After the coated seedlings were allowed to dry for 48 hours, they were potted and placed in a greenhouse. The plants were then evaluated to determine: (1) the percent of the plants surviving the 48 hour drying period; (percent survival or survival rate); (2) the percent dieback/plant; and (3) new root growth. New root growth was evaluated on a scale of 0–5, where 0 equals no new root growth, and 5 equals new roots forming a large root mass. It has been observed that excessive water stress causes a reduction in new root growth.

The results of the whole-plant experiments (Table 4) show that the coating compositions of the present invention are superior to previous antitranspirant compositions. Specifically, the present coating composition reduced water loss in Norway maple seedlings from about 1.5 to about 2.4 times the values obtained with the previous antitranspirants listed in Table 3. The vapor transmission rate values in Table 4 are expressed in the units: g H$_2$O.g FW$^{-1}$.48 h$^{-1}$. These values refer to the weight of water lost during a 48 hour drying period. "FW" is the fresh weight of the plant material. The values were determined by comparing the weight of fresh plant tissues at time 0 hrs. and the weight of the same tissues after 48 hrs. of oven-drying at 65° F. The water vapor transmission rates were determined by the formula:

$$\text{Vapor tran. rate} = \frac{\text{Init. wt. (0 hrs.)} - \text{Final wt. (48 hrs.)}}{\text{Init. wt. (0 hrs.)} \times \text{Time}}$$

The average water vapor transmission rate for prior coating compositions was about 0.149 g H$_2$O.g FW$^{-1}$.48 h$^{-1}$, or 2.1 times the water vapor transmission for undiluted "MOISTURIN" coating composition (water vapor transmission rate = 0.072 g H$_2$O.g FW$^{-1}$.48 h$^{-1}$) and 1.1 times "MOISTURIN" coating composition applied as an emulsion (water vapor transmission rate = 0.136 g H$_2$O.g FW$^{-1}$.48 h$^{-1}$).

The coating compositions of the present invention reduced the water loss in Washington hawthorns from about 1.8 times to about 2.7 times the values obtained with the antitranspirant compositions listed in Table 4. The average water transmission rate for Washington hawthorns coated with prior compositions was about 0.199 g H$_2$O.g FW$^{-1}$.48 h$^{-1}$, compared to 0.092 g H$_2$O.g FW$^{-1}$.48 h$^{-1}$ for undiluted "MOISTURIN" coating composition (a reduction in water vapor transmission rate of 2.2) and 0.130 g H$_2$O.g FW$^{-1}$.48 h$^{-1}$ for "MOISTURIN" coating composition applied as an emulsion (a reduction in water vapor transmission rate of 1.5).

Moreover, the coating compositions of the present invention substantially increased the survival rate of the plants tested (Table 4). The Washington hawthorn control seedlings had a survival rate of only about 10 percent. However, hawthorn seedlings treated with the plant coating compositions of the present invention had an increased survival rate of up to about 80 percent. Some of the previous antitranspirant compositions listed in Table 3, such as "BPC #1" composition and "SHIELD-BRITE AP-50C" composition also had survival rates of about eighty percent. However, both "BPC #1" composition and "SHIELD-BRITE AP-50C" composition had dieback ratings of 88 percent, and new root growth ratings of 2.3 and 1.6, respectively. The Washington hawthorn seedlings treated with undiluted "MOISTURIN" coating composition had a percent dieback rating of 25 percent, and 43 percent with "MOISTURIN" coating composition applied as an emulsion. Hence, the dieback values for hawthorns treated with "MOISTURIN" coating compositions are about 3.5 times less than Washington hawthorns treated with the next-best available coating compositions. Percent dieback values are significant because they typically correlate with survival rate, especially when plants are subjected to water stress periods greater than those discussed herein.

The hawthorn seedlings had new root growth ratings of 3.4 and 3.2 for the "MOISTURIN" coating composition emulsion and full-strength compositions, respectively. "BPC #1" composition, the best antitranspirant agent tested in terms of root growth other than the "MOISTURIN" coating compositions, had a root rating of 2.4, or from about 1.4 to about 2.0 times worse than Washington hawthorns treated with the present coating compositions.

The results for the Norway maple test are similar to those discussed above for the Washington hawthorn. A number of the maple seedlings coated with prior coating compositions had survival rates of 80 percent or greater. However, it can be seen that the coating compositions of the present inventions are superior to these previous antitranspirant coating compositions when the dieback values and root-growth ratings of plants are compared. Specifically, Norway maple seedlings coated with "MOISTURIN" coating compositions, either full strength or as an emulsion, had zero percent dieback apparent after 48 hours The next closest competitor, "FRESH-COTE CW1" composition, had a dieback rating of nearly 15 percent. The average dieback rating for compounds other than the "MOISTURIN" coating compositions was about 37 percent.

Furthermore, the new root growth ratings for the Norway maple seedlings were significantly improved when the coating compositions of the present invention were used compared to the values obtained for prior coating compositions. For instance, the next-closest competitor in terms of plant survival, "FRESH-COTE CW1" composition, had a root rating of about 1.7, whereas the Norway maples coated with "MOISTURIN" coating compositions had an average root rating of about 4.3, or greater than 2.5 times the root value for the seedlings coated with "FRESH-COTE CW1" composition.

The data presented in Tables 3 and 4 therefore demonstrate the effectiveness of the plant coating compositions of the present invention. Surprisingly, the results are dramatically superior to previous coating compositions, especially when survival rate, percent dieback and new root growth are also compared in addition to water vapor transmission values. Moreover, in similar tests with large hawthorn trees and with other plant materials such as conifer seedlings, Christmas trees, perennials and annuals, the coating compositions of the present invention greatly reduced water loss and improved the survival of the plant materials tested. In all tests conducted, the coating compositions were not toxic to foliage, stems or roots and allowed some gas exchange to occur.

TABLE 4

Water loss and survival of maple and hawthorn seedlings treated with antidesiccant compounds prior to 48 h air drying.[z,y]

| Treatment | Water Loss[x] | % Survival[w] | % Dieback[v] | Root Rating[u] |
|---|---|---|---|---|
| Norway Maple | | | | |
| control | 0.186 a | 80 | 52 a | 2.8 ab |
| BPC #1 | 0.173 ab | 100 | 29 ab | 3.3 ab |
| DECCO C | 0.162 abc | 90 | 34 ab | 2.9 ab |
| DECCO A | 0.161 abc | 100 | 28 ab | 3.5 ab |
| SHIELD BRITE AP-50C | 0.158 abcd | 90 | 38 ab | 2.3 ab |
| MOISTURIN (emulsion) | 0.136 bcd | 100 | 0 b | 4.1 b |
| SHIELD BRITE C-280 | 0.128 cd | 100 | 54 a | 3.3 ab |
| FRESH-COTE CW1 | 0.112 d | 100 | 14 ab | 1.7 a |
| MOISTURIN (full strength) | 0.072 e | 100 | 0 b | 4.5 b |
| Washington Hawthorn | | | | |
| control | 0.279 a | 10 | 99 a | 0.0 a |
| DECCO C | 0.248 ab | 50 | 95 a | 1.0 ab |
| DECCO A | 0.235 bc | 70 | 94 a | 1.5 abcd |
| SHIELD BRITE AP-50C | 0.199 cd | 80 | 88 a | 1.6 abcd |
| FRESH-COTE CW1 | 0.179 de | 50 | 87 a | 1.1 ab |
| SHIELD BRITE C-280 | 0.175 de | 70 | 93 a | 1.2 abc |
| BPC #1 | 0.161 ef | 80 | 88 a | 2.3 bcd |
| MOISTURIN (emulsion) | 0.130 f | 80 | 43 b | 3.4 d |
| MOISTURIN (full strength) | 0.092 9 | 80 | 25 b | 3.2 cd |

TABLE 4-continued

Water loss and survival of maple and hawthorn seedlings treated with antidesiccant compounds prior to 48 h air drying.[z,y]

| Treatment | Water Loss[x] | % Survival[w] | % Dieback[v] | Root Rating[u] |
|---|---|---|---|---|

[z]Water loss during 48 h air-drying at 23 ± 2° C., 47 ± 5% RH.
[y]Mean separation within columns by Tukey's multiple range test, P = 0.05.
[x]g water loss · g $FW^{-1} \cdot 48 \, h^{-1}$.
[w]% survival: number of plants which grew/total number of of plants (n = 10).
[v]% disback per plant: 0 = budbreak at the top of the stem, 100 = dead.
[u]Rating: 0 = no new roots, 5 = new roots forming a large root mass.

Having illustrated and described the principles of the invention and its preferred embodiments, it should be apparent to those skilled in the art that the invention can be modified in arrangement and detail without departing from such principles. We claim all modifications coming within the spirit and scope of the following claims.

We claim:

1. A process for reducing the rate of water loss in plants, the process comprising applying to a surface of a plant a sufficient amount of a composition to reduce the plant's water vapor transmission rate to less than about 0.15 g $H_2O$. g $FW^{-1}.48 \, h^{-1}$, the composition comprising water and from at least about forty weight percent of a polymer material having monomer subunits of the formula $H_2C = CR_1, R_2$, wherein $R_1$ is selected from the group consisting of halogens, and $R_2$ is selected from the group consisting of hydrogen and halogens.

2. The process according to claim 1 wherein the monomer subunit is vinyl chloride.

3. The process according to claim 1 wherein the monomer subunit is vinylidene chloride.

4. The process according to claim 2 wherein the weight percent of the vinyl chloride polymer material is from about forty percent to about ninety-five percent.

5. The process according to claim 4 wherein the composition comprises from about eighty-five to about ninety-five weight percent vinyl chloride polymer material.

6. The process according to claim 5 wherein one application of the composition to the surface of the plant provides a water vapor transmission rate that is less than 0.1 g $H_2O$.g $FW^{-1}.48 \, h^{-1}$.

7. The process according to claim 4 wherein the composition comprises from about forty to about forty-five weight percent vinyl chloride polymer material.

8. A process for reducing water loss in plants, the process comprising applying to a surface of a plant a sufficient amount of a composition to reduce the plant's water vapor transmission, the composition comprising water and a polymer material having monomer subunits of the formula $H_2C = CR_1R_2$, wherein both $R_1$ and $R_2$ are independently selected from the group consisting of halogens.

9. A process for reducing water stress in plants, the process comprising applying to a surface of a plant a sufficient amount of a composition to reduce the plant's water vapor transmission wherein the composition comprises:

(1) a polymer material having monomer subunits of the formula $H_2C = CR_1R_2$ wherein $R_1$ is selected from the group consisting of halogens, and $R_2$ is selected from the group consisting of hydrogen and halogens;

(2) a viscosity enhancing agent;

(3) a defoaming agent;
(4) a coalescing agent;
(5) a surfactant; and
(6) water.

10. The process according to claim 9 wherein the monomer subunit is vinyl chloride, the viscosity enhancing agent is a urethane copolymer, the defoaming agent is silica, the coalescing agent is 2,2,4-trimethyl-1,3-pentanediol monoisobutyrate, and the surfactant is a polyoxyethylene-polyoxypropylene copolymer.

11. The process according to claim 10 wherein the plant's water vapor transmission rate is less than 0.1 g $H_2O.g$ $FW^{-1.48}$ $h^{-1}$ and the composition comprises:
   (1) from about eighty-five to about ninety-five weight percent of the vinyl chloride polymer material;
   (2) from about 0.5 to about 1.0 weight percent of the urethane copolymer;
   (3) from about 0.5 to about 1.0 weight percent of the silica;
   (4) from about 1.5 to about 2.5 weight percent of the 2,2,4-trimethyl-1,3-pentanediol monoisobutyrate;
   (5) from about 0.5 to about 1.5 weight percent of the polyoxyethylene-polyoxypropylene copolymer; and
   (6) water.

12. The process according to claim 10 wherein the water vapor transmission rate is less than 0.15 g $H_2O$. g $FW^{-1.48}$ $h-1$ and the composition comprises;
   (1) from about forty to about forty-five weight percent of the vinyl chloride polymer material;
   (2) from about 0.25 to about 0.5 weight percent of the urethane copolymer;
   (3) from about 0.25 to about 0.5 weight percent of the silica;
   (4) from about 0.75 to about 1.25 weight percent of the 2,2,4-trimethyl-1,3-pentanediol monoisobutyrate;
   (5) from about 0.25 to about 0.75 weight percent of the polyoxyethylene-polyoxypropylene copolymer; and
   (6) water.

13. The process according to claim 9 wherein the composition is applied to a plant seedling and including the step of replanting the seedling.

14. A liquid plant coating composition for reducing a plant's water vapor transmission rate to less than about 0.15 g $H_2O.g$ $FW^{-1.48}$ $h^{-1}$, the composition comprising water and from at least about forty weight percent of a polymer material having monomer subunits of the formula $H_2C=CR_1R_2$, wherein $R_1$ is selected from the group consisting of halogens, and $R_2$ is selected from the group consisting of hydrogen and halogens.

15. The coating composition according to claim 14 wherein the monomer subunit is vinyl chloride.

16. The coating composition according to claim 15 wherein the polymer material comprises from about forty to about eighty-five weight percent of the composition.

17. The coating composition according to claim 15 wherein the polymer material comprises from about eight-five to about ninety-five weight percent of the composition.

18. The coating composition according to claim 14 wherein the monomer subunit is vinylidene chloride.

19. The composition according to claim 14 wherein the composition further comprises a viscosity enhancing agent, a defoaming agent, a coalescing agent, and a surfactant.

20. The composition according to claim 19 wherein the monomer subunit is vinyl chloride, the viscosity enhancing agent is a urethane copolymer, the defoaming agent is silica, the coalescing agent is 2,2,4-trimethyl-1,3-pentanediol monoisobutyrate, and the surfactant is a polyoxyethylene-polyoxypropylene copolymer.

21. A plant coating composition comprising:
   a polymer material formed from monomers having the formula $H_2C=CR_1R_2$ wherein $R_1$ is selected from the group consisting of halogens, and $R_2$ is selected from the group consisting of hydrogen and halogens;
   a viscosity enhancing agent;
   a defoaming agent;
   a coalescing agent;
   a surfactant; and
   water.

22. The composition according to claim 21 wherein the polymer material is a vinyl chloride polymer, the viscosity enhancing agent is a urethane copolymer, the defoaming agent is silica, the coalescing agent is 2,2,4-trimethyl-1,3-pentanediol monoisobutyrate, and the surfactant is a polyoxypropylene-polyoxyethylene copolymer.

23. The composition according to claim 22 comprising:
   from about forty to about ninety-five weight percent of the vinyl chloride polymer material;
   from about 0.5 to about 1.0 weight percent of the urethane polymer;
   from about 0.3 to about 1.0 weight percent of silica;
   from about 1.0 to about 2.0 weight percent of a 2,2,4-trimethyl-1,3-pentanediol monoisobutyrate;
   from about 0.5 to about 1.0 weight percent of a polyoxypropylene-polyoxyethylene copolymer; and
   water.

24. A liquid plant coating composition comprising water and a polymer material having monomer subunits of the formula $H_2C=CR_1CR_1R_2$, wherein $R_1$ and $R_2$ are independently selected from the group consisting of halogens.

* * * * *